United States Patent
Bendahan et al.

(10) Patent No.: US 9,123,519 B2
(45) Date of Patent: Sep. 1, 2015

(54) METHODS AND SYSTEMS FOR TIME-OF-FLIGHT NEUTRON INTERROGATION FOR MATERIAL DISCRIMINATION

(71) Applicant: Rapiscan Systems, Inc., Torrance, CA (US)

(72) Inventors: Joseph Bendahan, San Jose, CA (US); Vladimir Solovyev, Fremont, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 144 days.

(21) Appl. No.: 13/907,811

(22) Filed: May 31, 2013

(65) Prior Publication Data

US 2013/0327948 A1     Dec. 12, 2013

Related U.S. Application Data

(60) Provisional application No. 61/654,656, filed on Jun. 1, 2012.

(51) Int. Cl.
| | |
|---|---|
| G01N 23/00 | (2006.01) |
| H01J 47/12 | (2006.01) |
| G01V 5/00 | (2006.01) |
| H05H 3/06 | (2006.01) |

(52) U.S. Cl.
CPC ............... *H01J 47/12* (2013.01); *G01V 5/0016* (2013.01); *H05H 3/06* (2013.01)

(58) Field of Classification Search
CPC .................................. H05H 6/00; H05H 3/06
USPC ....................... 250/390.04, 390.08
See application file for complete search history.

(56) References Cited

U.S. PATENT DOCUMENTS

| | | | |
|---|---|---|---|
| 3,374,355 A | 3/1968 | Parratt | |
| 3,914,614 A * | 10/1975 | Martone et al. | 378/147 |
| 4,975,917 A | 12/1990 | Villa | |
| 5,014,293 A | 5/1991 | Boyd | |
| 5,076,993 A * | 12/1991 | Sawa et al. | 376/159 |
| 5,181,234 A | 1/1993 | Smith | |
| 5,202,932 A | 4/1993 | Cambier | |
| 5,224,144 A | 6/1993 | Annis | |

(Continued)

FOREIGN PATENT DOCUMENTS

| | | |
|---|---|---|
| EP | 1526392 | 4/2005 |
| WO | 2005121756 A2 | 12/2005 |

(Continued)

OTHER PUBLICATIONS

International Search Report for PCT/US13/43801, Dec. 6, 2013.

(Continued)

*Primary Examiner* — David Porta
*Assistant Examiner* — Abra Fein
(74) *Attorney, Agent, or Firm* — Novel IP

(57) ABSTRACT

The present invention provides a Time-of-Flight based neutron inspection system. The system employs a collimated beam of fast neutrons for targeted interrogation of suspect areas in cargo. Elemental composition is determined as a function of depth. Analysis is then used to determine the presence of contraband. The system may be used for secondary inspection for material discrimination to reduce false alarm rate and high cost and time associated with manual unpacking.

16 Claims, 5 Drawing Sheets

(56) References Cited

U.S. PATENT DOCUMENTS

| | | |
|---|---|---|
| 5,548,630 A | 8/1996 | Hell |
| 5,602,894 A | 2/1997 | Bardash |
| 5,763,903 A | 6/1998 | Mandai |
| 5,764,683 A | 6/1998 | Swift |
| 5,854,531 A * | 12/1998 | Young et al. ............... 313/362.1 |
| 6,081,580 A | 6/2000 | Grodzins |
| 6,125,165 A | 9/2000 | Warburton |
| 6,216,540 B1 | 4/2001 | Nelson |
| 6,418,194 B1 | 7/2002 | McPherson |
| 6,421,420 B1 | 7/2002 | Grodzins |
| 6,542,580 B1 | 4/2003 | Carver |
| 6,605,473 B1 | 8/2003 | Hajduk |
| 7,099,434 B2 | 8/2006 | Adams |
| 7,151,447 B1 | 12/2006 | Willms |
| 7,277,526 B2 | 10/2007 | Rifkin |
| 7,420,175 B2 | 9/2008 | Chu |
| 7,461,032 B2 | 12/2008 | Heaton |
| 7,622,726 B2 | 11/2009 | Zillmer |
| 7,809,104 B2 | 10/2010 | Foland |
| 7,844,028 B2 | 11/2010 | Korsunsky |
| 7,860,213 B2 | 12/2010 | Akery |
| 7,978,804 B2 | 7/2011 | Groves |
| 2002/0150194 A1* | 10/2002 | Wielopolski et al. ......... 376/160 |
| 2004/0086078 A1 | 5/2004 | Adams |
| 2005/0226383 A1 | 10/2005 | Rifkin |
| 2006/0176998 A1 | 8/2006 | Korsunsky |
| 2007/0140423 A1 | 6/2007 | Foland |
| 2007/0160176 A1* | 7/2007 | Wada ............................ 376/158 |
| 2007/0241283 A1* | 10/2007 | Chu et al. .................... 250/358.1 |
| 2008/0296519 A1* | 12/2008 | Larsen et al. ............... 250/515.1 |
| 2009/0001277 A1* | 1/2009 | Payne et al. ............... 250/370.12 |
| 2009/0238336 A1 | 9/2009 | Akery |
| 2009/0257555 A1 | 10/2009 | Chalmers |
| 2010/0025573 A1* | 2/2010 | Hahto et al. ................... 250/251 |
| 2010/0289409 A1* | 11/2010 | Rosenthal ................ 315/111.81 |

FOREIGN PATENT DOCUMENTS

| | | |
|---|---|---|
| WO | 2011069024 A1 | 6/2011 |
| WO | 2013181646 A2 | 12/2013 |

OTHER PUBLICATIONS

International Atomic Energy Agency, Manual for troubleshooting and upgrading of neutron generators. Nov. 1996 [retreived on Sep. 16, 2013]. Retrieved from the Internet: <URL: http://www-pub.iaea.org/MTCD/publications/PDF/te_913_web.pdf> figures 149-150, pp. 200-203.

International Search Report for PCT/US10/58809; Rapiscan Systems Inc.; Apr. 19, 2011.

Search and Examination Report for Application No. GB1420349.1, dated Nov. 26, 2014.

Office Action dated Dec. 10, 2012 for U.S. Appl. No. 12/959,356.

* cited by examiner

Top View

|  | C | H | O | N | C/O | N*O/C^2 |
|---|---|---|---|---|---|---|
| Cocaine | 68.5 | 7.0 | 20.5 | 4.0 | 3.3 | 0.02 |
| C4 | 22 | 4 | 40 | 35 | 0.6 | 2.89 |
| Fish | 19.9 | 10.5 | 66.2 | 3.5 | 0.3 | 0.58 |
| Produce | 5.9 | 10.6 | 83.5 | 0.0 | 0.1 | 0.00 |
| Paper | 47.0 | 6.0 | 44.0 | 0.0 | 1.1 | 0.00 |

FIG. 3

METHODS AND SYSTEMS FOR TIME-OF-FLIGHT NEUTRON INTERROGATION FOR MATERIAL DISCRIMINATION

CROSS-REFERENCE TO RELATED APPLICATIONS

The present application claims priority to and relies upon U.S. Provisional Patent Application No. 61/654,656, entitled "Methods and Systems for Time-of-Flight Neutron Interrogation for Material Discrimination" and filed on Jun. 1, 2012, which is herein incorporated by reference in its entirety.

FIELD

The present specification generally relates to the field of radiant energy imaging systems for detecting concealed objects, and more specifically to a system that uses neutron interrogation to inspect objects and provide an enhanced level of material characterization.

BACKGROUND

Physical shipment of materials, including the shipment of mail, merchandise, raw materials, and other goods, is an integral part of any economy. Typically, the materials are shipped in a type of shipping container or cargo box, which are generally transported via semi-trailers, large trucks, and rail cars as well as inter-modal containers that can be carried on container ships or cargo planes. Such shipping or cargo containers, however, are also sometimes used for illegal transportation of contraband. Detection of these threats requires a rapid, safe and accurate inspection system.

High-energy x-ray inspection is employed worldwide to detect contraband including drugs, currency, weapons and manifest violations. Contraband detection is typically performed by analyzing images for anomalies. Oftentimes when anomalies are identified as potential contraband, manual labor intensive and time-consuming unpacking is required. In some cases, equipment has to be damaged to determine whether contraband is actually present. Unfortunately, these anomalies may be produced by the natural variation of benign cargo, therefore leading to a false alarm situation where the manual inspection was unnecessary.

Known scanning processes for inspection of containerized cargo include X-ray scanning, chemical analysis of vapour emitting from the cargo, listening to sound from the cargo to detect living objects and eventually interventional manual search of the cargo by one or more security officials. In some systems, neutrons are employed in secondary inspection techniques and methods to detect and/or clear the presence of explosives and other materials. For example, Rapiscan Systems, Inc. has a Vehicle Explosive Detection System (VEDS) that employs a moderated $^{232}$Cf spontaneous fission source or an Electronic Neutron Generator (ENG) such as d-D or d-T to produce neutrons for inspecting a cargo container. In most cases, the neutrons are mainly uncollimated, impinge upon a large area of the container, are not depth sensitive and provide limited elemental information. Therefore, these systems can detect medium amounts of contraband and are limited to some types of materials.

One of the advantages of employing neutrons is that their interaction with matter results in gamma rays. These gamma rays are characteristic of the elements that produced them and therefore, can be used to deduce the elemental composition. When an object is interrogated with neutrons, gamma-ray signals are produced from different parts of the object; signal mixing is reduced by determining the position of mono-energetic neutrons as a function of time. This, in turn, yields gamma ray information as a function of time. As the speed of neutrons is known, the location of where the gamma rays were produced can be computed. This provides a determination of the elemental composition of the scanned area as a function of depth, with little mixing of signal from other areas.

With continuous wave (CW) sources—which produce radiation continuously, or pulsed at micro-second intervals, it is very difficult to determine the location where gamma rays are produced. There is a superposition from gamma rays produced in the front, the center and the back of the object and the deduced elemental composition is mixed. For example, if there is an amount of cocaine located in the center of a paper-loaded container, the gamma rays will present mainly from the paper and minimally from the cocaine, in which case, the cocaine may remain undetected. This is because the neutrons will interact more at the front than at the center due to attenuation. Since there is no time (depth) information, the elemental signal from cocaine (very little signal) is summed up with the elemental signal of paper (more abundant signal). For example, the signal of cocaine is C=4 and O=1 (C/O=4). The signal of paper is C=10 and O=10 (C/O=1). The measured signal is C=14 and O=11 with a C/O of 1.3. However, if time (depth) information is present, information from the front, center, and back is separated into discrete, detectable signals. Thus, TNA (Thermal Neutron Analysis) does not work well because of the mixing of signals as a function of depth.

By way of example, in Pulsed Fast Neutron Analysis (PFNA) technology, a high-energy pulsed deuteron beam impinges on a deuterium target to produce an intense nano-second pulsed neutron beam, which allows for determination of the elemental content of the area being inspected. The cross section (x-y) mapping is obtained by the use of collimation and the depth (z) map is obtained using time-of-flight (ToF) technology. PFNA can be used for primary inspection and/or for secondary inspection. In the secondary approach, a primary system (PFNA, x-ray or other) identifies areas suspected of containing contraband which are then inspected with a collimated neutron beam. Although PFNA is a very powerful technology, a system based on this technology is large and expensive, which limits its deployment.

Similarly, Associated Alpha-Particle Imaging (API) employs a partially collimated neutron beam to inspect an object, whereby an elemental map of the object can be determined. The cross-sectional elemental map is obtained by detecting the associated alpha particle direction, which is emitted 180 degrees relative to the direction of the emitted neutron. The depth map is also obtained using ToF technology but instead of using a pulsed-neutron beam, the detection of the alpha particle provides the starting time. When deuterons from the generator hit the tritium target, the nuclear reaction results in an alpha particle and a neutron, produced 180 degrees from each other. The alpha particle is detected first because the alpha detector is proximate. Thus, it can be used to start the clock to determine where the associated neutron is. If at t=0 the neutron is at 10 cm, at t=1 ns, it will be at 15 cm and at t=2 ns, it will be at 20 cm, because neutrons move at approximately 5 cm/ns.

Due to the random coincidences of the alpha particle and neutron-induced gamma ray measurements, the resultant signals are affected by a high background that limits the maximum neutron output. This requires lowering the neutron output to a level where this background is low, but results in long inspection times, reducing the throughput.

While d-D and d-T neutron generators employing techniques similar to PFNA and API have been used, they have not been widely deployed due to either size and cost limitations, or long inspection times as a result of low neutron yield. A d-D neutron generator employs a deuteron beam which impinges on a gas deuterium target to produce a neutron beam at a beam energy of ~8.5 MeV. A d-T neutron generator uses the deuterium ($^2$H)—tritium ($^3$H) reaction to generate neutrons. Deuterium atoms in the accelerated beam fuse with deuterium and tritium atoms in the target to produce neutrons and alpha particles.

There is therefore a need for a compact, low-cost, high-intensity, material-specific primary or secondary inspection system and method suitable for deployment. As a secondary inspection method and system, there is a need for that method and system to clear or confirm alarms of a primary system in a relatively short inspection time with high throughput.

Therefore, what is needed is a compact, high-yield and deployable targeted neutron inspection system that results in short inspection times.

SUMMARY

The present specification describes a Time-of-Flight based neutron inspection system. The system employs a collimated beam of fast neutrons to interrogate suspect cargo to determine the elemental information as a function of depth. The elemental composition is then analyzed to determine the presence of contraband.

In one embodiment, a nano-pulsed, compact and high-yield d-T generator is employed.

In one embodiment, the system may be used for primary inspection, and implemented in portal, gantry or mobile configurations.

In another embodiment, the system may be used for secondary inspection for material discrimination to reduce the false-alarm rate, the high cost and time associated with manual unpacking. In one embodiment, an object under inspection is identified as containing a potential threat by a primary system or by an operator and is sent to the system of present invention for secondary inspection. In one embodiment, the primary system targets a small area within the object under inspection.

In yet another embodiment, an API generator with appropriate collimation is employed for secondary inspection. Targeting a small area allows for increasing the intensity of the API generator because the intensity that was previously used for interrogating a large area is now concentrated to a smaller spot, thus increasing the neutron output to a level where background is low and allows for shortened inspection time.

In one embodiment, the present specification describes a system for inspection of a suspect area in an object, comprising: a nano-second pulsed deuteron generator, said generator comprising an ion source to produce a beam of deuterium ions, and an ion filter, chopper and buncher for shaping the beam of deuterium ions into a narrow pulse width; a tritium target, which produces pulsed neutrons on being impinged by a pulsed beam of deuterium ions; a movable collimator to aim the pulsed neutrons at the suspect area; gamma-ray detectors to detect gamma rays produced after the interaction of pulsed neutrons with the suspect area; and a processing unit that analyzes Time-of-Flight (ToF) data from the detectors to determine materials in the suspect area. In one embodiment, the nano-second pulsed deuteron generator generates at least $10^9$ neutrons/second. In one embodiment, the processing unit uses ToF data to map signals from gamma-ray detectors into the elements of suspect area as a function of depth.

In one embodiment, the current of deuteron beam impinging on the tritium target is in the range of 100 μA. In one embodiment, the accelerating voltage of the beam is in the 100 to 300 kV range. In one embodiment, the ion source is a positive ion source.

In one embodiment, the tritium target comprises multiple targets. In another embodiment, the tritium target comprises a rotating target. Further, the tritium target is located at approximately the same height as the location of one of the sources in the primary system.

In one embodiment, the neutron generator is shielded to reduce dose outside the collimated beam and reduce gamma-ray background. Further, the shielding has a total thickness of approximately 75 cm.

In another embodiment, the present specification describes a system for inspection of a suspect area in an object, said suspect area being in the range of a few tens of centimeters, the system comprising: a d-T neutron generator, that produces neutrons and corresponding alpha particles; a neutron beam collimator to direct the neutrons at the suspect area, wherein said collimator is shielded; an alpha-particle detector placed 180-degrees relative to the suspect area to detect alpha particles and determine the time of generation of neutrons, wherein the alpha-particle detector is collimated to substantially the same angular opening as the neutron beam collimator; gamma-ray detectors to detect gamma rays produced after the interaction of neutrons with the suspect area, wherein said gamma ray detectors are shielded to prevent thermal and epi-thermal capture; and a processing unit to determine the elemental composition of the suspect area as a function of depth based on the time of generation of the neutrons and the time spectrum of the gamma rays produced.

In one embodiment, the borated material is borated polyethylene.

In one embodiment, the total neutron output of the neutron generator is in the range of $10^9$ neutrons per second.

In one embodiment, the size of the beam that impinges on the target is at least 1 cm, when a high deuteron beam current is used.

In one embodiment, the alpha-particle detector is placed at a distance in the range of 25 cm from target. In one embodiment, the alpha detector comprises of a multi-segmented detector.

In one embodiment, the neutron generator rotates along its long axis to aim neutrons at the suspect area. In one embodiment, the collimated beam is translated vertically to aim neutrons at the suspect area. In another embodiment, the collimated beam is rotated about its long axis to aim neutrons at the suspect area.

In one embodiment, the total overall length of the collimator is at least 75 cm.

In one embodiment, the neutron generator is shielded to reduce dose outside the collimated beam and to reduce background. Further, the shielding has a total thickness of approximately 50 cm.

In one embodiment, either system is used for secondary inspection, after inspection by a primary inspection system. In one embodiment, the system is based on a primary inspection subsystem and a secondary inspection subsystem and wherein suspect areas are identified by primary system or an operator, and wherein an algorithm is used to determine an optimal position and rotation angle of the object under inspection for inspecting the suspect areas with collimated neutrons.

The aforementioned and other embodiments of the present shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 2b is a schematic diagram of an exemplary shielding and collimating apparatus as employed in the neutron inspection system shown in in FIG. 2a;

FIG. 2c illustrates an end view of the time-of-flight neutron inspection system shown in FIG. 2a;

FIG. 3 is a table illustrating elemental composition information and corresponding ratios of exemplary materials that can be detected by the system of present invention.

DETAILED DESCRIPTION

Figure 1:
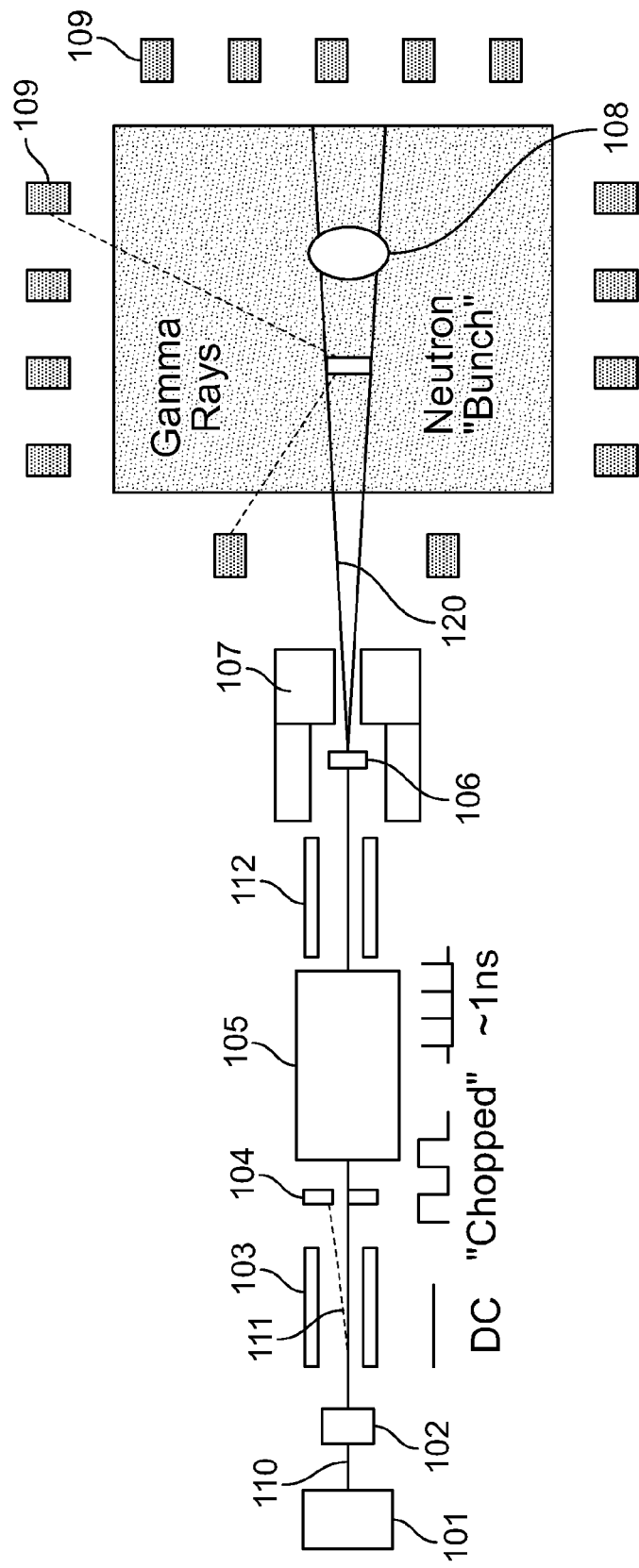
FIG. 1 illustrates a schematic diagram of a time-of-flight neutron inspection system based on the d-T reaction in accordance with one embodiment of the present specification, where a pulsed beam is employed.

The present specification is directed towards a Time-of-Flight (ToF) based neutron inspection system. More specifically, the present specification is directed towards systems and methods for detecting contraband and threats in cargo by use of a high-energy ToF-based neutron system with a collimated beam. In one embodiment, the system of the present invention employs a collimated beam of fast neutrons to interrogate suspect cargo to determine the elemental composition as a function of depth. The characteristic elemental composition is then analyzed to determine the presence of contraband.

One of the advantages of employing neutrons is that their interaction with matter results in gamma rays. These gamma rays are characteristic of the elements that produced them and therefore, can be used to deduce the elemental composition. Thus, when an object is interrogated with neutrons, gamma-ray signals are produced from different parts of the object; signal mixing is reduced by determining the position of mono-energetic neutrons as a function of time. This, in turn, yields gamma ray information as a function of time. As the speed of neutrons is known, the location of where the gamma rays were produced can be computed. This provides a determination of the elemental composition of the scanned area as a function of depth, with little mixing of signal from other areas. Generally, this is accomplished by determining the neutron position using nano-second pulsed neutron or associated alpha particle generators in novel methods, both of which are described in the present specification.

In one embodiment, a nanosecond-pulsed d-T Time-of-Flight (ToF) based neutron inspection system is employed and may be used for primary inspection, and implemented in portal, gantry or mobile configurations for detection of neutron-containing contraband.

In another embodiment, an API generator is employed. Using a collimator to restrict or direct the neutron beam to target a small area allows for increasing the intensity of the API generator because the intensity that was previously used for interrogating a large area is now concentrated to a smaller spot. This increases the number of neutrons that arrive at this smaller spot to a level at which the signal-to-background ratio is high, on the order of approximately $10^9$ neutrons/second, thus allowing for shortened inspection time. Thus, the intensity is on the order of 10 to 20 times greater than typical API generators (which operate in an intensity range of $5 \times 10^7$ to $5 \times 10^8$ neutrons per second before random coincidence results in a too-high background). Further, the collimator of the present specification has a small opening to restrict the neutron beam and is very well-shielded. Still further, the present specification employs shielding around the source and detector as well.

In one embodiment, the system may be used for secondary inspection for material discrimination to reduce the false-alarm rate, the high cost and time associated with manual unpacking. In one embodiment, an object under inspection is identified as containing a potential threat by a primary system and is sent to the system of present invention for secondary inspection. Thus, in one embodiment, the system described in the present invention scans a small area of the object that has been identified by a primary system or by an operator as suspect or possibly containing contraband or a threat.

In one embodiment, the system detects but is not limited to the detection of carbon, nitrogen, oxygen, chlorine, phosphorus, sodium, iron and other elements as a function of depth. The system performs elemental analysis to detect drugs, chemical weapons, and other contraband and in addition, performs cargo-manifest verification. Other gamma rays characteristic of elements such as hydrogen and chlorine associated with slow neutrons can also be detected to provide additional information of the cargo but without position information.

The system of the present specification is coupled to at least one display, which displays information about the inspection process and data, by means of a GUI. The system further comprises at least one processor or processing unit to control the operation of the entire system and its components. It should further be appreciated that the at least one processor is capable of processing programmatic instructions, has a memory capable of storing programmatic instructions, and employs software comprised of a plurality of programmatic instructions for performing the processes described herein. In one embodiment, the at least one processor is a computing device capable of receiving, executing, and transmitting a plurality of programmatic instructions stored on a volatile or non-volatile computer readable medium.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In a first embodiment, the system described in the present specification advantageously uses a nano-second pulsed d-T neutron generator. The d-T neutron generator uses the deuterium ($^2$H)-tritium ($^3$H) reaction to generate neutrons. Deuterium atoms in the accelerated beam fuse with deuterium and tritium atoms in the target to produce neutrons and alpha particles. Referring back to the PFNA technology described above, a 6 MeV pulsed deuteron beam impinges on a gas deuterium target to produce an intense nano-second pulsed neutron beam at a beam energy of ~8.5 MeV. These reactions are characterized by the following equations:

$$d+t \rightarrow n+{}^4\text{He En}=14.2 \text{ MeV} \qquad (1)$$

$$d+d \rightarrow n+{}^3\text{H Q}=3.27 \text{ MeV} \qquad (2)$$

While the 8.5 MeV neutrons are more prolific and have advantages over 14 MeV neutrons, to create 8.5 MeV neutrons, a much larger and more expensive system is required. Thus, a far more compact and less expensive system is required to produce 14 MeV neutrons.

FIG. 1 shows a schematic diagram of the system that produces pulsed neutrons for scanning suspect areas of an object. Referring to FIG. 1, an ion source 101 produces a beam of deuterium ions 110 and accelerates them, with a low voltage in one embodiment, towards an ion selector 102. In one embodiment, the ion source is a positive ion source to produce high beam current. The ion selector 102 filters unwanted ions, preventing ions with multiple energies from being present in the beam which will result in an increase in the current and sputtering of the target and small increase in neutron yield. Since ions can carry either a positive or negative charge and have different speeds, the goal is to filter out either the positive or negative ions and keep only one type of charge, depending upon the type of accelerator employed. The filter also reduces the number of ions hitting the various components to minimize neutron production in the accelerator, which would require extensive shielding.

The filtered beam 111 is periodically deflected using a deflector 103, which allows a fraction of the beam to pass through a slit 104. The slit 104 thus acts as a beam chopper. The beam chopper is used to pulse the beam (coarse pulsing). The coarsely pulsed chopped beam is then bunched (or shaped) using a high-power bunching device 105, which accelerates the trailing ions and decelerates the leading ions. This results in the trailing ions and leading ions catching up to one another, otherwise known as "bunching" together. In one embodiment, the beam is bunched to a pulse time in the range of 1 ns. Keeping the time of the pulsing in nano-second (ns) range is critical. The resulting neutrons move at a speed of ~5 cm/ns; therefore, the time scale to get the resolution in the range of a few centimeters has to be in nanoseconds. If the pulse time is in microseconds, it would yield a resolution in meters, thereby resulting in the mixing of signals from various parts of the object and chances of contraband remaining undetected. The beam is then sent through a post-acceleration stage using hardware 112 that allows for additional acceleration of the deuterium ion beam which increases its energy. In one embodiment the accelerating voltage is in the range of 100 to 300 kV.

The beam then impinges onto a tritium target 106. In one embodiment, the current of the deuteron beam impinging on the tritium target is in a range of up to 500 μA. The resulting pulsed neutrons are shielded and narrowly collimated, using a collimator 107, into a beam 120 directed to the suspect area 108. After interaction of neutrons with the suspect area 108, the resultant gamma rays produced by inelastic interaction with the neutrons are detected using an array of gamma-ray detectors 109. Time-of-Flight (ToF) electronics and a processing unit map the signals from gamma-ray detectors into elements as a function of depth.

One of ordinary skill in the art would appreciate that in order to avoid servicing the system at unacceptably short intervals a long life target is used. In one embodiment, the target is made of multiple targets where a replacement can be put into position when one target is partially depleted, without requiring servicing the system. In one embodiment, the system uses a rotating target.

The d-T generator of the present invention is a compact, high output generator and more suitable for deployment in various applications, as compared to bulky prior-art generators. In one embodiment, the neutron generator is well-shielded to reduce dose outside the collimated beam and reduce gamma-ray background.

In a second embodiment, the system of present invention employs a d-T neutron generator with an alpha detector to determine the position of neutrons as a function of time. The d-T reaction produces both a 14 MeV neutron and an alpha particle that travels in a direction exactly 180 degrees opposite to the produced neutron.

A conventional problem with alpha particle imaging (API) is that if the intensity of the deuteron beam is increased to get more neutrons, the alpha particles start arriving too close to each other and the identification of the neutrons gets confusing due to random coincidences of the alpha particles and neutron-induced gamma ray measurements. A produced neutron can collide with shielding materials and produce gamma rays, which are detected at random times and result in increased background in the time area of interest. The resultant signals are affected by a high background that limits the maximum neutron output. Conventionally, this requires lowering the neutron output to a level where this background is low, but results in long inspection times. Thus, use of API to image large cargo areas has been limited due to the intensity, as the output is low and it results in unacceptably long times to image a large object.

Specifically, random coincidence events increase as the square of neutron intensity, $a^2 I^2$, where 'a' is a parameter that depends on background and is derived experimentally. Background comes from mainly two sources: 1) time correlated background (TCB), which is produced by fast-neutron interactions and 2) time uncorrelated background (TUB), which is produced by thermal neutron interaction with surrounding matter. Therefore, in order to reduce random coincidence, these sources of background must be decreased. As described above, leaking neutrons can interact in other parts of the object being inspected and also with surrounding materials, producing a TCB. Eventually, some of these neutrons slow down and are captured, producing a TUB. Similarly, gamma rays produced by the neutron interaction in the shielding/collimator can increase TCB. Of particular interest is the high energy 4.44 MeV gamma ray from carbon for which sufficient shielding must be placed to virtually eliminate it. Other gamma rays produced by thermal neutron capture in the shielding material, such as 2.23 MeV from hydrogen, can also escape and increase the TUB, so sufficient shielding must be incorporated to prevent this too.

The present specification describes a method in which only small areas of the object are scanned at a time. This is achieved by collimating the neutron beam into a cone beam or small rectangular beam to project to the size of the area of interest. Thus, the optimal API source shielding/collimator configuration of the present specification is designed such that it results in very low leakage of neutrons and gamma rays, except for the neutrons that travel through the collimated aperture. Critical design specifications include using large amounts of shielding with appropriate materials and a long collimator.

Figure 2A:
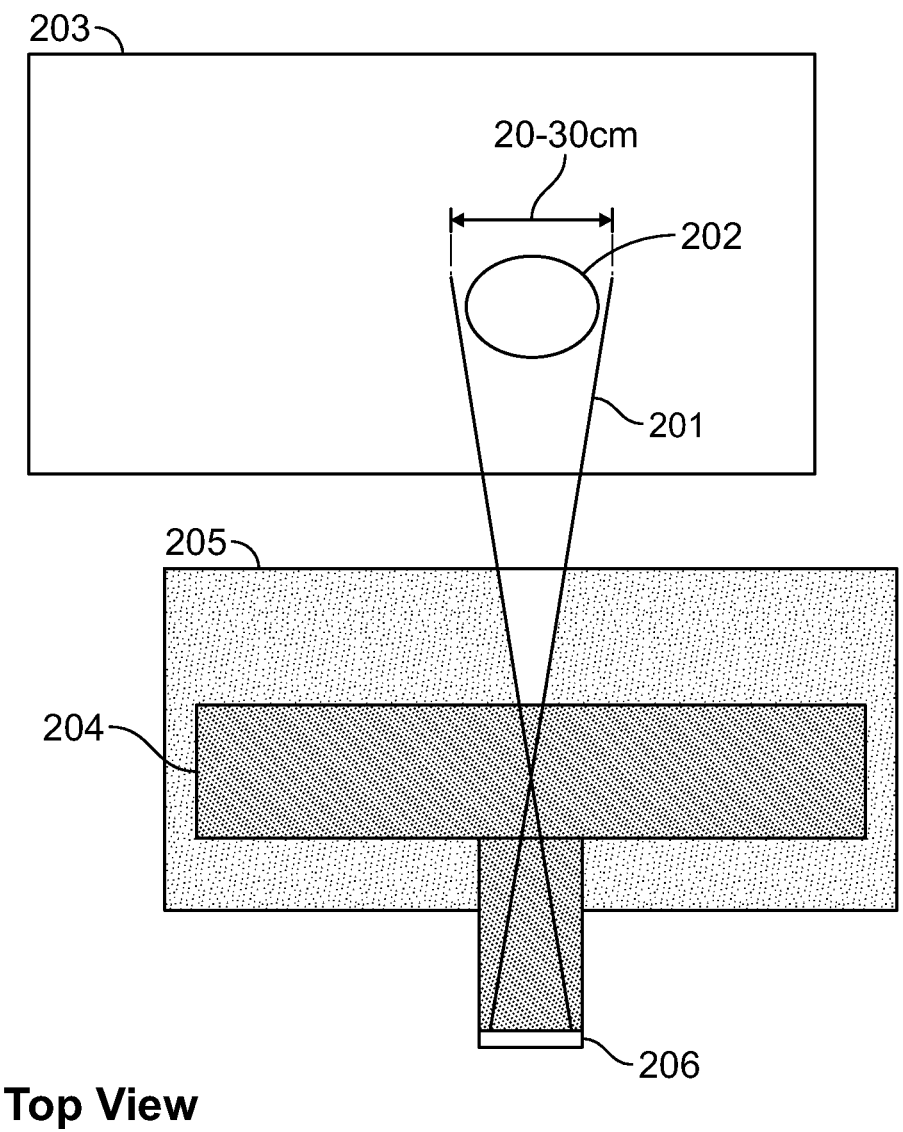
FIG. 2a illustrates a top view of a time-of-flight neutron inspection system in accordance with one embodiment of the present specification, in which an associated alpha particle imaging (API) system is employed.

FIG. 2a illustrates a schematic diagram of the top view of a system with a high-yield API generator. Referring to FIG. 2a, a highly collimated neutron beam 201 is used to inspect an area 202, which may be a part of cargo 203, for example. The beam 201 is generated by the API generator 204, which is accompanied by an appropriate shielding and collimating apparatus 205 (shown in FIG. 2b). The neutron beam is well-collimated so that it inspects a small area of the container, such as in the range of a few tens of centimeters at the center of a cargo container. In one embodiment, the neutron generator rotates about its long axis to aim neutrons at the suspect area. However, in order to maintain the focal-spot position (the point where neutrons originate) in the same place to avoid issues of parallax (described below with respect to FIG. 4), it is preferred to rotate the collimator. To inspect different parts of cargo, in one embodiment, the collimator beam itself needs to be directed towards the suspect areas of interest. In one embodiment, the collimated beam is moved in a vertical direction. In one embodiment, the collimated beam is rotated.

Figure 2B:
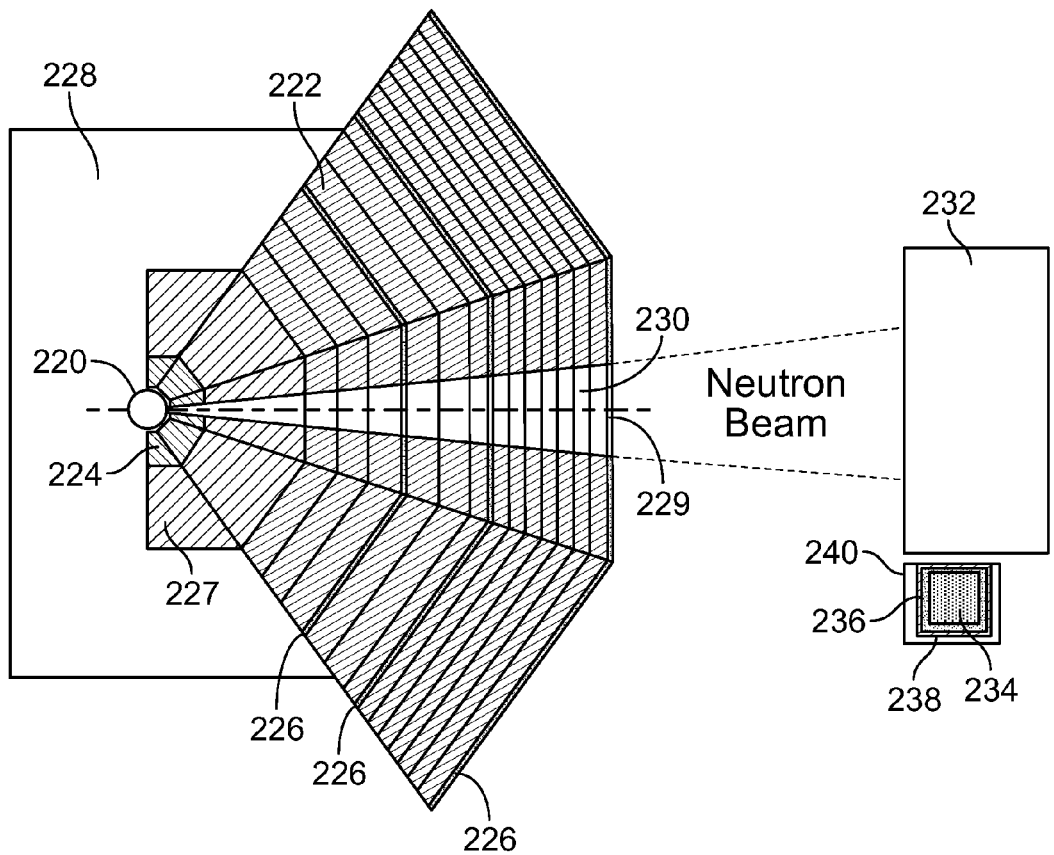

Referring now to FIG. 2b, collimation of the neutron beam from neutron source 220 is typically achieved using a shielding structure, which, in one embodiment, is a combination of a borated material 222 (such as, but not limited to borated polyethylene), tungsten 224 and lead 226. It should be understood that although the present specification describes the use of borated polyethylene, any number of borated materials that achieves the objective of the present invention may be employed. A portion of the tungsten layer 224 can be replaced with a metal layer 227, to reduce cost, where the metal layer comprises, but is not limited to iron or copper. In one embodiment, the borated polyethylene layer 222 has a boron content of 2-5%. In one embodiment, the borated polyethylene layer 22 has a thickness of approximately 15 cm. In one embodiment, layers of lead 226 are interleaved between the layers of borated polyethylene 222 to reduce gamma rays produced in the shielding that could add to the random coincidence and increase the background. In one embodiment, the layers of lead 226 have a thickness of 2 cm. In another embodiment, a lead layer can be added to the end of the collimator, versus being interleaved with the borated polyethylene layer, however, the collimator would have a larger weight than compared with the interleaved approach. In another embodiment, an alternate high-Z material (for example, bismuth) can be used in place of lead.

Additional shielding materials 228 surround the collimator to reduce the neutron leakage in other directions that can also produce background with the surroundings. The shielding in areas that do not intersect the object to be inspected 232 and the detectors 234 is reduced for weight and cost considerations. The amount of shielding that exists in these areas to prevent leaking neutrons from interacting with the surrounding regions that produce background gamma rays depends on the system configuration, but is typically on the order of 50 cm. The shielding is comprised of materials similar to the collimator—tungsten, followed by steel or copper (although more tungsten is preferred), followed by borated poly/lead layers.

In one embodiment, the total overall length of the collimator is at least 75 cm. In another embodiment, more steel/copper is employed for shielding, resulting in a collimator design longer than 75 cm. In one embodiment, the collimator ranges from 75 to 100 cm in length. This, however, is a trade-off between competing considerations of cost, size, and performance.

In one embodiment, a layer of B10 or equivalent 229 is placed close to the exit of the collimator 230 to eliminate any thermal neutrons surviving the collimator and not absorbed by the shielding.

The gamma-ray detectors 234 must also be well-shielded to prevent thermal and epi-thermal capture. In one embodiment, borated material 238, such as $B_4C$, is used for shielding. In one embodiment, 15 mm of $B_4C$ is employed. In one embodiment, approximately 3 mm of lead shielding 236 is used between the borated shielding 238 and the detector 234 to absorb the 478 keV gamma rays from thermal capture in boron. Additional thermal-neutron shielding 240 is added to structural materials supporting the system components, concrete and other surrounding material to reduce the TUB.

Knowing the time of generation of the neutrons and thus, timing the generated spectrum of the gamma rays, the elemental composition of the scanned object as a function of depth can be determined.

The cross-section elemental map of the inspected area is obtained by detecting the direction of the associated alpha particle and using that information to determine the direction and position of the emitted neutron, which is emitted 180 degrees relative to the alpha particle, as described above. A detector provides the alpha particle with a time of generation as well as the direction relative to the target. Further, in detecting the alpha particle trajectory, the time of generation of the accompanying neutron as well as its direction are determined, since its line of travel is opposite to that of the alpha particle. When deuterons from the generator hit the tritium target, the nuclear reaction results in an alpha particle and a neutron, positioned 180 degrees from each other. The alpha particle is detected first because the alpha detector is proximate. Thus, it can be used to start the clock to determine where the associated neutron is. If at t=0 the neutron is at 10 cm, at t=1 ns, it will be at 15 cm and at t−2 ns, it will be at 20 cm, because neutrons move at 5 cm/ns. The fast neutrons thus produced are therefore defined as "tagged" (by the alpha particle), in time as well as in direction.

Referring back to FIG. 2a, an alpha particle detector 206 is placed at a distance and at 180 degrees relative to the target. In a preferred embodiment, the alpha detector 206 is also collimated to have the same angular range as the collimated beam, thus the angular coverage of the alpha detector corresponds to the neutron beam. For this purpose, the size of the alpha detector, in one embodiment, is no bigger than that required to capture the associated neutrons going in the opposite direction. A smaller angle would result in not all of the neutrons in the collimated beam being tagged. Since the number of alpha particles to avoid random coincidences is fixed, when a small area is inspected, there is a much larger neutron flux. This allows getting results in a short time compatible with deployed systems. In one embodiment, the alpha particle detector is a multi-segmented detector.

The size of the beam on target (focal spot) can be greater than 1 cm, when a high deuteron beam current is used (for higher output). The large focal spot is required to maintain the current density low while employing a large deuteron current needed to produce a high neutron output. In this case, if the alpha detector is too close, alpha particles associated with the neutrons going in a larger angle than what the collimator allows will also be detected. This increases the random coincidences resulting in a higher background. The placement of the alpha detector 206 at a relatively large distance ensures that the fuzziness of the neutron-beam is avoided, which is generally associated with the uncertainty of the angular spread of the neutron due to the large size of the deuteron focal spot. In one embodiment, the detector is placed at a distance greater than ~25 cm to reduce the effect of the size of the focal spot on the direction of the neutrons.

In one embodiment, API generator employed in the present invention provides a high neutron yield. In one embodiment, the total neutron output is approximately in the range of or greater than $10^9$ neutrons/sec. This allows for determining the presence of contraband or clearing cargo in approximately one minute or less.

Figure 2C:
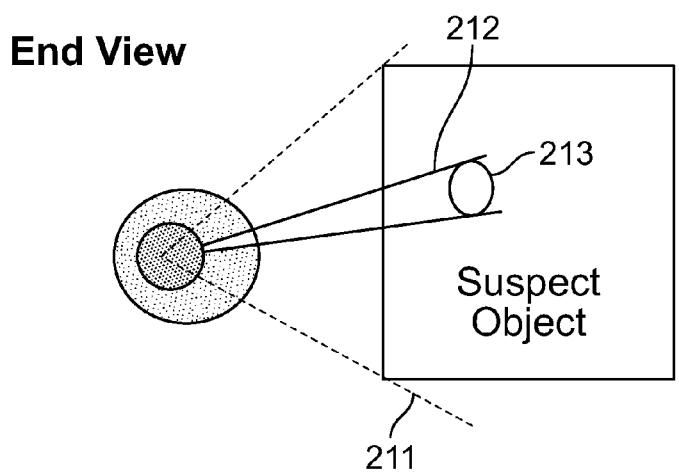

FIG. 2c illustrates an end view of the API system. Referring to FIG. 2c, the broad neutron beam 211 that is generated in typical applications using neutron beam-alpha particle imaging is shown. Further, the narrow, highly-collimated beam 212 generated by the present system 215 that is used to accurately scan the target 213 is also shown.

Further, the small-angle alpha-particle detector, the highly-collimated neutron beam and the well shielded neutron generator, detectors and collimator of the present invention result in a low random coincidence background that enables getting a high signal-to-background ratio.

The system of present invention is capable of detecting a variety of contraband in an accurate and reliable manner. FIG. 3 is a table illustrating the elemental composition of some of the materials that the system is able to identify. Columns 301, 302, 303 and 304 indicate Carbon, Hydrogen, Oxygen and Nitrogen content, respectively, of various materials. Columns 305 and 306 indicate the carbon-to-oxygen ratio (C/O) and $N*O/C^2$ ratio for a given material, respectively. These ratios are especially useful in discriminating and identifying different materials. For example, a high a carbon-to-oxygen ratio (C/O) 305 would indicate the presence of cocaine, heroin and other drugs; while a high $N*O/C^2$ ratio 306 would indicate the presence of most explosives. Other features can be used to identify these and other materials of interest.

In one embodiment, the system of present invention may be operated to inspect selected areas of the cargo for cargo-manifest verification. In this case, the elemental composition of the scanned areas is compared to the elemental composition of the claimed manifest to provide a probability that the manifest is correct.

In a preferred embodiment, the position of the tritium target should be at the same height as the height of the focal-spot source of the primary system. If the primary system has multiple sources, then the location would be at the same position as one of the sources. This is preferred avoid the uncertainties of parallax and would allow for interrogating the suspect area with a single directed scan.

Figure 4:
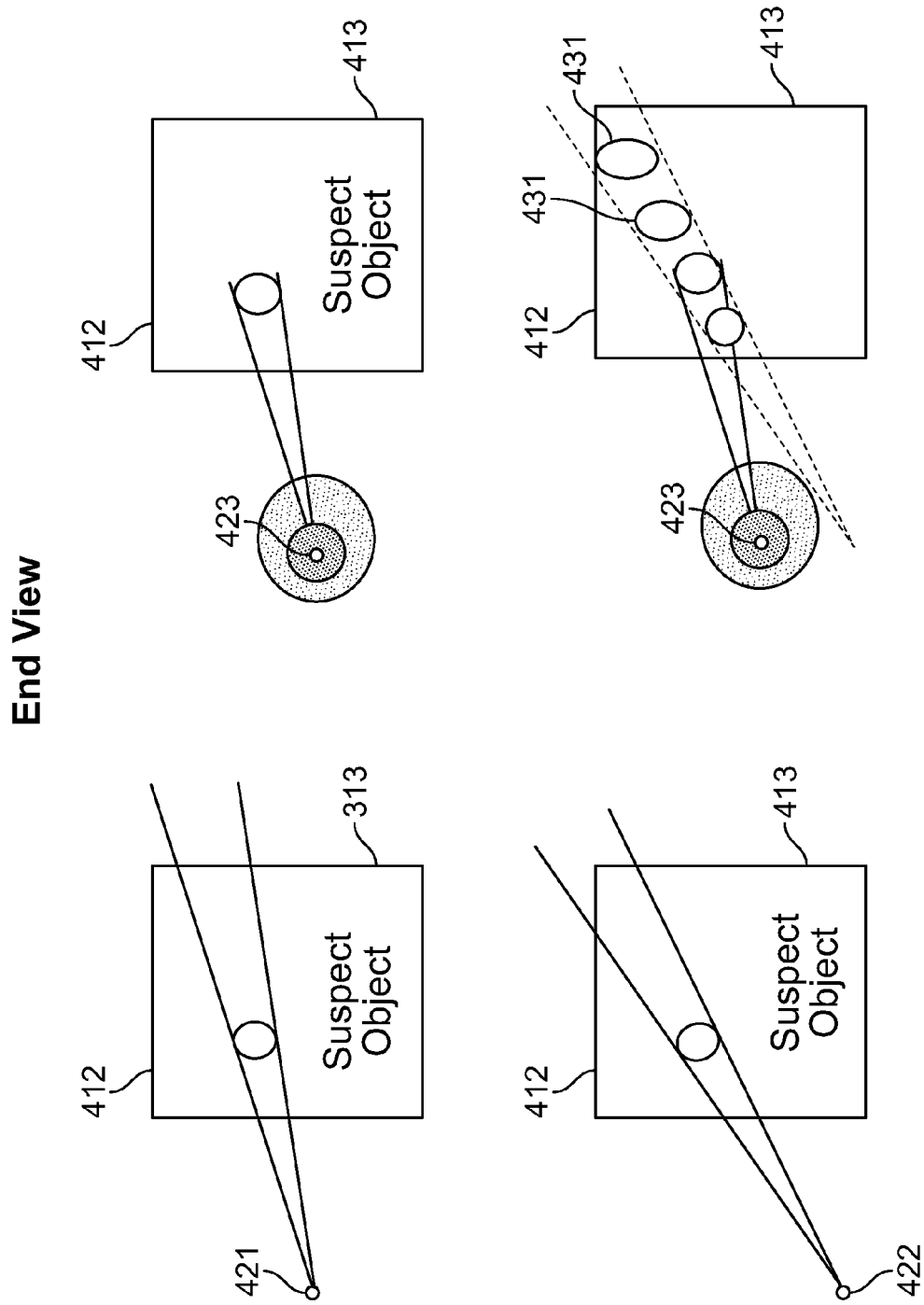
FIG. 4 illustrates the effect of the uncertainty in parallax for having different source heights in primary and secondary scans.

FIG. 4 shows the effect of not having the primary and secondary inspection sources at the height. Source 422 of the primary system is at different height as source 423 of the secondary system. The projected image of the primary system indicates that the suspect object could be in any depth along the projection lines. However, since secondary source 423 is at the different location, the system must inspect all the probable locations 431 to avoid missing the suspect object.

If the primary system produces a 3D image, there is not a strong preference for the position of the tritium target. In this case, the operator or automated detection algorithm would indicate the suspect area in 3D and the beam will be directed to this area. In an additional embodiment, the object will be rotated to an optimal angle and translated in such a way to get the highest signal, and the area will be interrogated. Multiple interrogations at different angles are also possible.

The neutron-based inspection system of the present invention may be used for mobile applications as well as where the system requires to be relocated for inspection. The system is also suitable for gantry and portal configurations, and for cargo as well as vehicle inspections.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive.

We claim:

1. A system for inspecting a suspect area in an object, comprising:
    a nano-second pulsed deuteron generator configured to generate at least $10^9$ neutrons/second, said nano-second pulsed deuteron generator comprising an ion source to produce a pulsed beam of deuterium ions and an ion filter, chopper and buncher for shaping the pulsed beam of deuterium ions into a narrow pulse width;
    a tritium target, which produces pulsed neutrons upon being impinged by the pulsed beam of deuterium ions and wherein a current of the pulsed beam of deuteron ions impinging on the tritium target is in the range of 100 µA;
    a movable collimator configured to generate a collimated beam of pulsed neutrons and aim the pulsed neutrons at the suspect area;
    gamma ray detectors to detect gamma rays produced after an interaction of pulsed neutrons with the suspect area; and
    a processing unit that analyzes time-of flight (ToF) data from the gamma ray detectors to determine identities of materials in the suspect area.

2. The system of claim 1 wherein the processing unit uses said ToF data to map signals from gamma ray detectors into elements of the suspect area as a function of depth.

3. The system of claim 1, wherein an accelerating voltage is in a 100 to 300 kV range.

4. The system of claim 1, wherein the ion source is a positive ion source.

5. The system of claim 1, wherein the tritium target comprises multiple targets.

6. The system of claim 1, wherein the tritium target comprises a rotating target.

7. A system for inspecting a suspect area in an object, comprising:
    a pulsed deuteron generator configured to generate neutrons, said pulsed deuteron generator comprising an ion source to produce a pulsed beam of deuterium ions, wherein the pulsed deuteron generator is shielded to reduce a dose outside the collimated beam of pulsed neutrons and reduce gamma ray background and wherein said shielding has a total thickness of approximately 75 cm;
    a tritium target, which, when impinged upon by the pulsed beam of deuterium ions, generates pulsed neutrons;
    a movable collimator configured to generate a collimated beam of pulsed neutrons directed toward the suspect area;
    gamma ray detectors to detect gamma rays produced after an interaction of the pulsed neutrons with the suspect area; and
    a processing unit that analyzes time-of flight (ToF) data from the gamma ray detectors to determine identities of materials in the suspect area.

8. A system for inspecting a suspect area in an object, the system comprising:
- a d-T neutron generator configured to produce neutrons and corresponding alpha particles;
- a neutron beam collimator to collimate the neutrons into a collimated beam and direct the neutrons at the suspect area, wherein said neutron beam collimator is shielded, using layers comprising at least one of borated polyethylene, tungsten, steel, copper and lead, to reduce neutron leakage and gamma rays produced in the collimator;
- an alpha-particle detector placed 180-degrees relative to the suspect area to detect alpha particles and determine a time of generation of said neutrons, wherein the alpha-particle detector is collimated to substantially a same angular opening as the neutron beam collimator;
- gamma-ray detectors configured to detect gamma rays produced after an interaction of neutrons with the suspect area, wherein said gamma ray detectors are shielded to prevent thermal and epi-thermal capture; and
- a processing unit to determine an elemental composition of the suspect area as a function of depth based on the time of generation of the neutrons and a time spectrum of the gamma rays produced.

9. The system of claim 8, wherein a total neutron output of the neutron generator is in a range of $10^9$ neutrons per second.

10. The system of claim 8, wherein a size of the collimated beam that impinges on the suspect area is at least 1 cm, when a high deuteron beam current is used.

11. The system of claim 8, wherein the alpha-particle detector is placed at a distance in the range of 25 cm from the object.

12. The system of claim 8, wherein the alpha detector comprises a multi-segmented detector.

13. The system of claim 8, wherein the d-T neutron generator rotates along its long axis to aim neutrons at the suspect area.

14. The system of claim 8, wherein the d-T neutron generator comprises shielding to reduce a dose outside the collimated beam and wherein said shielding has a total thickness of approximately 50 cm.

15. The system of claim 8, wherein a total overall length of the collimator is at least 75 cm.

16. The system of claim 8, wherein the system comprises a primary inspection subsystem and a secondary inspection subsystem, wherein suspect areas are identified by the primary inspection subsystem system and wherein the system determines an optimal position and rotation angle of the object for inspecting the suspect areas with collimated neutrons.

* * * * *